US011613530B2

(12) United States Patent
Wang (10) Patent No.: US 11,613,530 B2
(45) Date of Patent: Mar. 28, 2023

(54) THERMALLY ACTIVATED DELAYED FLUORESCENT MOLECULAR MATERIAL, METHOD FOR SYNTHESIZING THE SAME, AND ORGANIC ELECTROLUMINESCENT DEVICE

(71) Applicant: WUHAN CHINA STAR OPTOELECTRONICS SEMICONDUCTOR DISPLAY TECHNOLOGY CO., LTD., Hubei (CN)

(72) Inventor: Yanjie Wang, Wuhan (CN)

(73) Assignee: WUHAN CHINA STAR OPTOELECTRONICS SEMICONDUCTOR DISPLAY TECHNOLOGY CO., LTD., Hubei (CN)

( * ) Notice: Subject to any disclaimer, the term of this patent is extended or adjusted under 35 U.S.C. 154(b) by 489 days.

(21) Appl. No.: 16/629,972

(22) PCT Filed: Oct. 24, 2019

(86) PCT No.: PCT/CN2019/112904
§ 371 (c)(1),
(2) Date: Feb. 10, 2020

(87) PCT Pub. No.: WO2020/220611
PCT Pub. Date: Nov. 5, 2020

(65) Prior Publication Data
US 2020/0339546 A1    Oct. 29, 2020

(30) Foreign Application Priority Data

Apr. 29, 2019    (CN) .......................... 201910352671.7

(51) Int. Cl.
*C07D 403/14*    (2006.01)
*C07D 407/14*    (2006.01)
(Continued)

(52) U.S. Cl.
CPC .......... *C07D 403/14* (2013.01); *C07D 407/14* (2013.01); *C07D 409/14* (2013.01);
(Continued)

(58) Field of Classification Search
CPC ............... H01L 51/006; H01L 51/0072; H01L 51/0073; H01L 51/0074
See application file for complete search history.

(56) References Cited

FOREIGN PATENT DOCUMENTS

| CN | 102958906 A | 3/2013 |
| CN | 103709153 A | 4/2014 |

(Continued)

OTHER PUBLICATIONS

Machine translation of CN 108864068.*
(Continued)

*Primary Examiner* — Anthony Ho
(74) *Attorney, Agent, or Firm* — PV IP PC; Wei Te Chung; Ude Lu (57) ABSTRACT

A thermally activated delayed fluorescent molecular material, a method for synthesizing the same, and an organic electroluminescent device are provided. The thermally activated delayed fluorescent molecular material includes an electron donor and an electron acceptor containing an indenyl group. A phenyl group in diphenylamine or triphenylamine in a donor molecule is replaced with an indenyl group, so that the electron-donating ability of the donor is increased, and the non-radiative transition rate is effectively suppressed, thereby increasing the photoluminescence quantum yield (PLQY) of the molecule. Further, the torsion angle between the electron donor and the electron acceptor is also increased, while the electron cloud overlap between the highest occupied molecular orbital (HOMO) and the lowest unoccupied molecular orbital (LUMO) is reduced, thereby obtaining a smaller $\Delta E_{ST}$ value.

7 Claims, 1 Drawing Sheet

(51) Int. Cl.
*C07D 409/14* (2006.01)
*H01L 51/00* (2006.01)
*H01L 51/50* (2006.01)

(52) U.S. Cl.
CPC ........ *H01L 51/006* (2013.01); *H01L 51/0061* (2013.01); *H01L 51/0072* (2013.01); *H01L 51/0073* (2013.01); *H01L 51/0074* (2013.01); *H01L 51/5012* (2013.01)

(56) References Cited

FOREIGN PATENT DOCUMENTS

| | | | |
|---|---|---|---|
| CN | 104725296 A | 6/2015 |
| CN | 106565720 A | 4/2017 |
| CN | 108864068 A | 11/2018 |
| CN | 109134446 A | 1/2019 |
| CN | 109651406 A | 4/2019 |
| CN | 110105262 A | 8/2019 |
| JP | 2002082461 A | 3/2002 |
| WO | 2011136482 A1 | 11/2011 |

OTHER PUBLICATIONS

PCT International Search Report for International Application No. PCT/CN2019/112904, dated Jan. 23, 2020, 6pp.
PCT Written Opinion for International Application No. PCT/CN2019/112904, dated Jan. 23, 2020, 12pp.
PCT International Preliminary Report on Patentability for International Application No. PCT/CN2019/112904, dated Nov. 2, 2021, 14pp.

\* cited by examiner

THERMALLY ACTIVATED DELAYED FLUORESCENT MOLECULAR MATERIAL, METHOD FOR SYNTHESIZING THE SAME, AND ORGANIC ELECTROLUMINESCENT DEVICE

FIELD OF INVENTION

The invention relates to the technical field of an organic photoelectric material, and particularly relates to a thermally activated delayed fluorescent single molecule white light material, a method for synthesizing the same, and an organic electroluminescent device.

BACKGROUND OF INVENTION

Organic light-emitting diodes (OLEDs), due to their advantages of active illumination, wide viewing angle, fast response speed, wide temperature adaptation range, low driving voltage, low power consumption, high brightness, simple production process, light and thin, and flexible display, etc., show great application prospects in the field of OLED display and lighting, and attract the attention of researchers and companies. At present, SAMSUNG and LG have implemented the OLEDs on mobile phones. In the OLED, the quality of a light emitting layer material is the decisive factor in whether the OLED can be industrialized or not. A typical light emitting layer material consists of main and guest light emitting materials, and the luminescence efficiency and lifetime of the light emitting material are two important indicators of the light emitting material. The early OLED light emitting materials were conventional fluorescent materials. Since a ratio of excitons in a singlet state to excitons in a triplet state in the OLED is 1:3, and the conventional fluorescent materials can only emit light using the singlet excitons, the quantum efficiency in the OLED theory of the conventional fluorescent materials is 25%. Metal complex phosphorescent materials are capable of achieving 100% utilization of the singlet excitons and the triplet excitons due to spin-orbit coupling effects of heavy atoms, and are also used in red and green OLED displays now. However, the phosphorescent materials usually use heavy metals, such as Ir, Pt, Os, and other precious metals, which are not only costly, but also highly toxic. In addition, efficient and long service life phosphorescent metal complex materials are still a great challenge. In 2012, Adachi et al. proposed a pure organic luminescent molecule with a "thermally activated delayed fluorescence" (TADF) mechanism, which allows the molecule to have a smaller difference between minimum singlet state and triplet energy level (singlet-triplet energy difference, $\Delta E_{ST}$) through a rational molecular design of the D-A structure, such that the triplet excitons can return to the singlet state through the reverse intersystem crossing (RISC), and then illuminate by the radiation transition to the ground state, so that the singlet and triplet excitons can be simultaneously utilized, and the utilization of the excitons can be achieved at 100% without the participation of the heavy metals. Also, TADF material has abundant structure designs, and most of its physical properties are easily adjusted to obtain an efficient and long service life organic luminescent material that meets the requirements.

SUMMARY OF INVENTION

Technical Problems

Most of the designs of the TADF molecule are D (donor)—A (acceptor) type structures. Further, the donor usually has a structure of diphenylamine, carbazole, and acridine or derivatives thereof. A torsion angle of the carbazole with the acceptor A is appropriate, but the electron-donating ability of the carbazole is too weak. The electron-donating ability of the diphenylamine is moderate, but the torsion angle with the acceptor A is too small. The electron-donating ability of the acridine is very strong, but the torsion angle with the receptor is too large. The large torsion angle will make RISC rate high, but the photoluminescence quantum yield (PLQY) of the material will decrease. If the electron donating ability is too weak, the charge transfer difference between D and A will be poor. The degree of HOMO and LUMO overlap between D and A is too large, resulting in a larger $\Delta E_{ST}$.

Technical Solutions

The technical problems to be solve in the present invention is to provide a thermally activated delayed fluorescent molecular material, a method for synthesizing the same, and an organic electroluminescent device. A phenyl group in diphenylamine or triphenylamine in a donor molecule is replaced with an indenyl group, so that the electron-donating ability of the donor is increased, and the non-radiative transition rate is effectively suppressed, thereby increasing the photoluminescence quantum yield (PLQY) of the molecule. Further, the torsion angle between the electron donor and the electron acceptor is also increased, while the electron cloud overlap between the highest occupied molecular orbital (HOMO) and the lowest unoccupied molecular orbital (LUMO) is reduced, thereby obtaining a smaller $\Delta E_{ST}$ value.

To solve the above problems, the present invention provides a thermally activated delayed fluorescent molecular material including an electron donor and an electron acceptor, wherein the electron acceptor contains an indenyl group.

Further, a molecular structural formula of the electron donor is selected from the group consisting of:

-continued

,

,

,

,

,

-continued

,

,

, and

.

Further, a molecular structural formula of the electron acceptor is selected from the group consisting of:

The present invention further provides a method for synthesizing a thermally activated delayed fluorescent molecular material including the following steps. A donor group material containing an indenyl group, an acceptor group material, and a solvent are placed into a reaction vessel to be sufficiently dissolved and mixed to obtain a first mixed solution, and air in the reaction vessel is replaced with argon gas. A catalyst is added into the reaction vessel to carry out a reflux reaction with the first mixed solution for 24 hours, and cooled to obtain a second mixed solution. The second mixed solution is extracted using dichloromethane three times, water washed three times, and dried by anhydrous sodium sulfate, filtered, and rotary dried to obtain a target compound. A column chromatography is performed on the target compound solution by using a 200 mesh to 300 mesh silica gel, rinsed with an eluent, and then separated and purified to obtain the thermally activated delayed fluorescent molecular material.

Further, the donor group material is 6-bromo-1-methyl-N,N-bis(1-methylindol-3-yl)indol-3-amine. The acceptor group material is 6-bromo-1-methyl-N,N-bis(1-methylindol-3-yl)indol-3-amine. The catalyst is tetrakis(triphenylphosphine)palladium. A molar ratio of the donor group material, the acceptor group material, and the catalyst is 10:10:0.6 to 10:10:0.3.

Further, the solvent is toluene and a sodium carbonate aqueous solution. A volume ratio of the toluene to the sodium carbonate aqueous solution is 1:1 to 5:2. The eluent is petroleum ether. The reaction vessel is a three-necked flask, and a volume of the three-necked flask is 200 ml to 300 ml.

The present invention further provides an organic electroluminescent device including the thermally activated delayed fluorescent molecular material.

Further, the organic electroluminescent device includes a first electrode; a hole injection layer is disposed on the first electrode; a hole transport layer is disposed on the hole injection layer; a light emitting layer is disposed on the hole transport layer, and a material of the light emitting layer includes the thermally activated delayed fluorescent molecular material; an electron transport layer is disposed on the light emitting layer; a second electrode is disposed on the electron transport layer.

Further, the first electrode is an anode, and a material used is indium tin oxide. The second electrode is a cathode, and a material used is one of lithium fluoride or aluminum.

Further, the light emitting layer further includes 1,3-bis (9H-carbazole-9-yl)benzene. A material of the hole injection layer is 2,3,6,7,10,11-hexacyanyl-1,4,5,8,9,12-hexaazatriphenylene. A material of the electron transport layer is 1,3,5-tris(3-(3-pyridyl)phenyl)benzene. A material of the hole transport layer is 4,4'-cyclohexyl bis[N,N-bis(4-methylphenyl)aniline].

Beneficial Effects

The present invention provides the thermally activated delayed fluorescent molecular material, the method for synthesizing the same, and the organic electroluminescent device. A phenyl group in diphenylamine or triphenylamine in a donor molecule is replaced with an indenyl group, so that the electron-donating ability of the donor is increased, and the non-radiative transition rate is effectively suppressed, thereby increasing the photoluminescence quantum yield (PLQY) of the molecule. Further, the torsion angle between the electron donor and the electron acceptor is also increased, while the electron cloud overlap between the highest occupied molecular orbital (HOMO) and the lowest unoccupied molecular orbital (LUMO) is reduced, thereby obtaining a smaller $\Delta E_{ST}$ value. The organic electroluminescent device of the present invention adopts the thermally activated delayed fluorescent molecular material prepared by the present invention, which has high luminous efficiency and long service life.

DESCRIPTION OF DRAWINGS

In order to more clearly illustrate the technical solutions in the embodiments of the present invention, briefly describes the accompanying drawings required for describing the embodiments used in the following embodiments will be apparent in the following description of the accompanying drawings are merely some embodiments of the present invention, for ordinary skill in the art, without creative efforts, you can obtain other drawings based on these drawings.

DETAILED DESCRIPTION OF PREFERRED EMBODIMENTS

The detailed description of the following embodiments is used for exemplifying the specific embodiments of the present disclosure by referring to the accompany drawings. The directional terms described by the present invention, such as upper, lower, front, back, left, right, inner, outer, side, etc., are only directions by referring to the accompanying drawings. The name of the component mentioned in the present invention, such as a first, second, etc., is only to distinguish different components, and can be better expressed. In the drawings, structure-like elements are labeled with like reference numerals.

Embodiments of the present invention will be described in detail herein with reference to the accompanying drawings. The present invention may be embodied in many different forms, and the present invention should not to be construed as being limited to the specific embodiments set forth herein. The embodiments of the present invention are provided to explain the practical application of the present invention so that those skilled in the art can understand various embodiments of the present invention and various modifications suitable for the specific intended applications.

The present invention provides a thermally activated delayed fluorescent molecular material including an electron donor and an electron acceptor, wherein the electron acceptor contains an indenyl group. The thermally activated delayed fluorescent molecular material has a structural formula: D-A. D is an electron donor, and A is an electron acceptor.

A molecular structural formula of the electron donor is selected from the group consisting of:

,

,

,

,

,

,

,

A molecular structural formula of the electron acceptor is selected from the group consisting of:

In order to more clearly explain the present invention, the thermally activated delayed fluorescent molecular material is further explained below in combination with a method for synthesizing the thermally activated delayed fluorescent molecular material of the present invention.

In an embodiment of the present invention, by taking the preparation of a target compound 1 (a thermally activated delayed fluorescent molecular material of the present invention) as an example, a preparation method of the thermally activated delayed fluorescent molecular material of the present invention is described in detail. A structural formula of the target compound is as follows:

The method for synthesizing the thermally activated delayed fluorescent molecular material of the present invention includes the following steps S1 to S4.

S1, a donor group material containing an indenyl group, an acceptor group material, and a solvent are placed into a reaction vessel to be sufficiently dissolved and mixed to obtain a first mixed solution, and air in the reaction vessel is replaced with argon gas.

The donor group material is 6-bromo-1-methyl-N,N-bis (1-methylindol-3-yl)indol-3-amine, and the acceptor group material is 6-bromo-1-methyl-N,N-bis(1-methylindol-3-yl) indol-3-amine.

The solvent is toluene and a sodium carbonate aqueous solution. A volume ratio of the toluene to the sodium carbonate aqueous solution is 1:1 to 5:2.

The reaction vessel is a three-necked flask, and a volume of the three-necked flask is 200 ml to 300 ml.

S2, a catalyst is added into the reaction vessel to carry out a reflux reaction with the first mixed solution for 24 hours, and cooled to obtain a second mixed solution.

The catalyst is tetrakis(triphenylphosphine)palladium. A molar ratio of the donor group material, the acceptor group material, and the catalyst is 10:10:0.6 to 10:10:0.3.

S3, the second mixed solution is extracted using dichloromethane three times, water washed three times, and dried by anhydrous sodium sulfate, filtered, and rotary dried to obtain a target compound.

S4, a column chromatography is performed on the target compound solution by using a 200 mesh to 300 mesh silica gel, rinsed with an eluent, and then separated and purified to obtain the thermally activated delayed fluorescent molecular material. The eluent is petroleum ether.

The thermally activated delayed fluorescent molecular material is prepared by the synthesis method of the present embodiment, which can effectively synthesize the thermally activated delayed fluorescent molecular material and improve the synthesis efficiency.

In order to verify whether the characteristics of the thermally activated delayed fluorescent molecular material of the present invention meet the requirements of the electroluminescent device, the thermally activated delayed fluorescent molecular material obtained by the preparation method of the present embodiment is subjected to spectral experiments and photophysical data detection in this embodiment. A fluorescence spectrum as shown in FIG. 1 and the photophysical data as shown in Table 1 are obtained.

Table 1 is the photophysical data of the thermally activated delayed fluorescent molecular material of the present invention.

| | PL Peak (nm) | $S_1$ (eV) | $T_1$ (eV) | $\Delta E_{ST}$ (eV) | PLQY (%) |
|---|---|---|---|---|---|
| Target compound | 635 | 2.35 | 2.26 | 0.09 | 89 |

Figure 1:
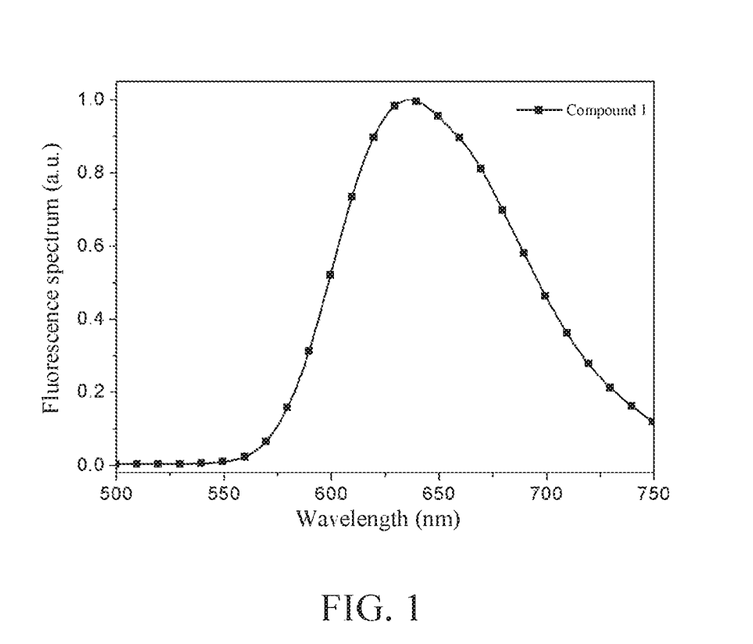
FIG. 1 is a photoluminescence spectrum of a target compound of the present invention.

It can be seen from FIG. 1, the target compound of the present invention has an effective wavelength in the range of 570 to 750 nm. Thus, the luminescence spectrum of the molecule can be adjusted within this range. It can be seen from Table 1, the thermally activated delayed fluorescent molecular material of the present invention has a smaller difference between minimum singlet state and triplet energy level (singlet-triplet energy difference, $\Delta E_{ST}$)

Figure 2:
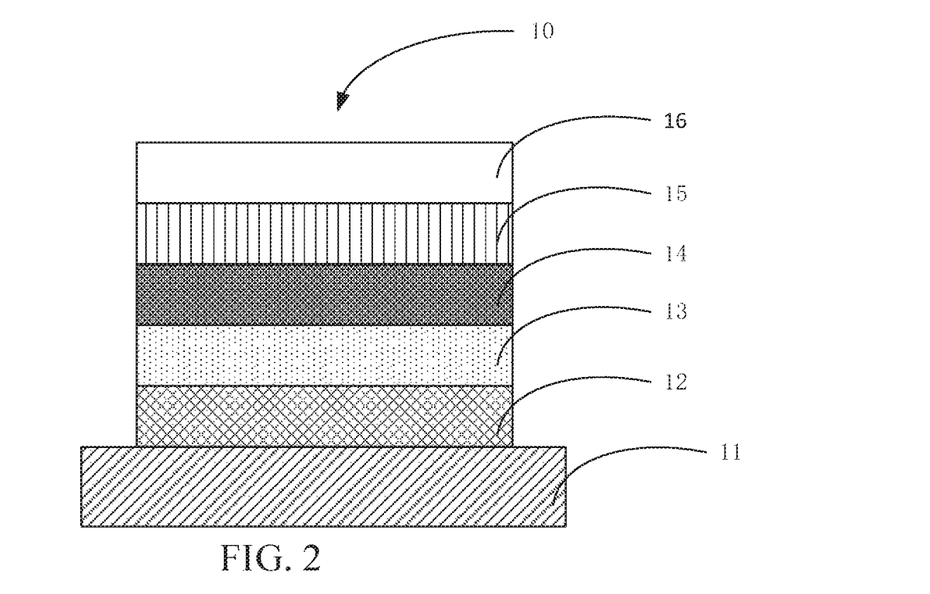
FIG. 2 is a schematic structural diagram of an organic electroluminescent device of the present invention.

As shown in FIG. 2, the present invention further provides an organic electroluminescent device including the thermally activated delayed fluorescent molecular material which can emit red light from the organic electroluminescent device.

Particularly, the organic electroluminescent device 10 includes a first electrode 11, a hole injection layer 12, a hole transport layer 13, a light emitting layer 14, an electron transport layer 15, and a second electrode 16.

The hole injection layer 12 is disposed on the first electrode 11. The hole transport layer 13 is disposed on the hole injection layer 12. The light emitting layer 14 is disposed on the hole transport layer 13. A material used for the light emitting layer 4 includes the thermally activated delayed fluorescent molecular material and 1,3-bis(9H-carbazol-9-yl)benzene as the main molecule, wherein the thermally activated delayed fluorescent molecular material is doped therein. The electron transport layer 15 is disposed on the light emitting layer 14. The second electrode 16 is disposed on the electron transport layer 15.

In the present embodiment, the first electrode 11 is an anode, and a material used is indium tin oxide. The second electrode 16 is a cathode, and a material used is one of lithium fluoride or aluminum. A material of the electron transport layer 15 is 1,3,5-tris(3-(3-pyridyl)phenyl)benzene, a material of the hole transport layer is 4,4'-cyclohexyl bis[N,N-bis(4-methylphenyl)aniline], and a material of the hole injection layer 12 is 2,3,6,7,10,11-hexacyanyl-1,4,5,8, 9,12-hexaazatriphenylene.

Table 2 is a performance data table of the organic electroluminescent device 10 using the target compound.

| Device | Maximum brightness (cd/m$^2$) | EL peak (nm) | Maximum external quantum efficiency (%) | Efficiency roll-off$^a$ (%) |
|---|---|---|---|---|
| Target compound | 3395 | 642 | 18 | 5.4 |

The electroluminescent device 10 of the present invention adopts the thermally activated delayed fluorescent molecular material in the light emitting layer 14 to effectively produce a red photoluminescence device, thereby improving the luminescence efficiency of the red electroluminescent device.

The present invention provides the thermally activated delayed fluorescent molecular material, the method for synthesizing the same, and the organic electroluminescent device. A phenyl group in diphenylamine or triphenylamine in a donor molecule is replaced with an indenyl group, so that the electron-donating ability of the donor is increased, and the non-radiative transition rate is effectively sup- pressed, thereby increasing the photoluminescence quantum yield (PLQY) of the molecule. Further, the torsion angle between the electron donor and the electron acceptor is also increased, while the electron cloud overlap between the highest occupied molecular orbital (HOMO) and the lowest unoccupied molecular orbital (LUMO) is reduced, thereby obtaining a smaller $\Delta E_{ST}$ value. The organic electroluminescent device of the present invention adopts the thermally activated delayed fluorescent molecular material prepared by the present invention, which has high luminescence efficiency and long service life.

The technical scope of the present invention is not limited to the above description of the contents. Any person who skilled in the art may deform and modify the embodiment of the present invention within the spirit and scope of the appended claims, but these deformation and modification belong to the protection scope of the present invention.

What is claimed is:

1. A thermally activated delayed fluorescent molecular material, comprising an electron donor and an electron acceptor, wherein the electron acceptor contains an indenyl group;

wherein a molecular structural formula of the electron donor is selected from one of following structural formulas:

,

,

,

-continued

,

,

,

,

,

-continued

2. The thermally activated delayed fluorescent molecular material according to claim 1, wherein a molecular structural formula of the electron acceptor is selected from the group consisting of 3. An organic electroluminescent device, comprising the thermally activated delayed fluorescent molecular material according to claim 1;
   wherein the organic electroluminescent device comprise:
   a first electrode;
   a hole injection layer disposed on the first electrode;
   a hole transport layer disposed on the hole injection layer;
   a light emitting layer disposed on the hole transport layer,
   a material of the light emitting layer comprising the thermally activated delayed fluorescent molecular material;
   an electron transport layer disposed on the light emitting layer; and
   a second electrode disposed on the electron transport layer;
   wherein the light emitting layer further comprises 1,3-bis(9H-carbazole-9-yl)benzene; a material of the hole injection layer is 2,3,6,7,10,11-hexacyanyl-1,4,5,8,9,12-hexaazatriphenylene; a material of the electron transport layer is 1,3,5-tris(3-(3-pyridyl)phenyl)benzene; and a material of the hole transport layer is 4,4'-cyclohexyl bis[N,N-bis(4-methylphenyl)aniline].

4. The organic electroluminescent device according to claim 3, wherein the first electrode is an anode, and a material used is indium tin oxide; the second electrode is a cathode, and a material used is one of lithium fluoride or aluminum.

5. A method for synthesizing a thermally activated delayed fluorescent molecular material, comprising:
 placing a donor group material containing an indenyl group, an acceptor group material, and a solvent into a reaction vessel to be sufficiently dissolved to obtain a first mixed solution, and replacing air in the reaction vessel with argon gas;
 adding a catalyst into the reaction vessel to carry out a reflux reaction with the first mixed solution for 24 hours, and cooling to obtain a second mixed solution;
 extracting the second mixed solution with dichloromethane three times, washing with water three times, and drying with anhydrous sodium sulfate, filtering, and rotary drying to obtain a target compound; and
 performing a column chromatography on a solution of the target compound by using a 200 mesh to 300 mesh silica gel, rinsing with an eluent, and then separating and purifying to obtain the thermally activated delayed fluorescent molecular material.

6. The method for synthesizing the thermally activated delayed fluorescent molecular material according to claim 5, wherein the donor group material is 6-bromo -1-methyl-N, N-bis(1-methylindol-3-yl)indol-3-amine; 17 the acceptor group material is 6-bromo -1-methyl-N,N-bis(1-methylindol-3-yl)indol-3-amine; the catalyst is tetrakis(triphenylphosphine)palladium; and a molar ratio of the donor group material, the acceptor group material, and the catalyst is 10:10:0.6 to 10:10:0.3.

7. The method for synthesizing the thermally activated delayed fluorescent molecular material according to claim 5, wherein the solvent is toluene and a sodium carbonate aqueous solution;
 a volume ratio of the toluene to the sodium carbonate aqueous solution is 1:1 to 5:2;
 the eluent is petroleum ether;
 and the reaction vessel is a three-necked flask, and a volume of the three-necked flask is 200 ml to 300 ml.

* * * * *